United States Patent [19]

Wexler et al.

[11] Patent Number: 4,936,837

[45] Date of Patent: Jun. 26, 1990

[54] ASEPTIC DRAINAGE OUTLET

[75] Inventors: Morton Wexler, Conyers, Ga.; Charles Huck, Gladstone, N.J.

[73] Assignee: C. R. Bard, Inc., Murray Hill, N.J.

[21] Appl. No.: 267,338

[22] Filed: Nov. 4, 1988

[51] Int. Cl.$^5$ .............................................. A61M 1/00
[52] U.S. Cl. ................................................... 604/326
[58] Field of Search ...................... 604/322, 326, 905; 285/319, 326, 174, 238, 319, 320, 174, 238; 128/769

[56] References Cited

U.S. PATENT DOCUMENTS

| | | | |
|---|---|---|---|
| 3,394,954 | 7/1968 | Sarns | 285/423 |
| 3,537,456 | 11/1970 | Harauteneian | 604/326 |
| 3,876,234 | 4/1975 | Harms | 285/38 |
| 4,270,778 | 6/1981 | Brownell | 285/305 |
| 4,326,516 | 4/1982 | Schultz et al. | 128/214 R |
| 4,329,967 | 5/1982 | Rogers et al. | 285/114 |
| 4,405,163 | 9/1983 | Voges et al. | 285/305 |
| 4,500,312 | 2/1985 | McFarlane | 604/263 |
| 4,573,981 | 3/1986 | McFarlane | 604/263 |
| 4,834,709 | 5/1989 | Banning et al. | 604/170 |

FOREIGN PATENT DOCUMENTS 538964  8/1941  United Kingdom ................ 285/320

*Primary Examiner*—J. L. Kruter
*Attorney, Agent, or Firm*—Dennison, Meserole, Pollack & Scheiner

[57] ABSTRACT

In a urinary drainage bag, a coupler for the outlet tube including a connector mounted on the discharge end of the outlet tube and defining a rigid extension thereof receivable within a bag-mounted housing. The connector includes spring arms having locking fingers releasably engagable behind a housing shoulder upon a seating of the connector body within the housing. The fingers are selectively released through a manual manipulation of the connector arms which provide for a positive handhold on the connector as the outlet tube is released.

3 Claims, 2 Drawing Sheets

ASEPTIC DRAINAGE OUTLET

BACKGROUND OF THE INVENTION

Flexible urine drainage bags, conventionally formed of peripherally sealed vinyl sheets, incorporate, in most instances, an elongate elastomeric outlet tube with a proximal end communicating with the interior of the bag at a low point therein. The distal end of the outlet tube is normally slidably received within a closed-end housing affixed to the bag above the proximal end of the tube.

In order to slidably engage the free distal end of the tube within the housing, the tube is flexed, normally adjacent the bag-engaged proximal end thereof, to align the free tube end with the housing. The received tube end is frictionally retained, both because of a snug engagement of the tube end within the housing and in light of pressure of the received tube end against the housing wall arising from the natural tendency for the tube to straighten or return to its unflexed position.

The distal end portion of the outlet tube is periodically disengaged from its secure "parked" position in the housing for an emptying of the vinyl drainage bag to a suitable drainage container. While the outlet tube is normally provided with a shut-off clamp, the distal end portion of the tube remains free and, upon release from the housing, tends to snap or spring outward due to the resilient nature of the outlet tube. Such a springing action results in an outward flicking or spraying of residual droplets of urine which accumulate within the outlet tube during normal usage of the drainage bag. Thus, the user or health care worker is exposed to such droplets which, not infrequently, fall both on the hands and the face and expose the individual to a great potential for contamination. This problem has become particularly acute in light of the increasing incidence of Acquired Immune Deficiency Syndrome (AIDS) and the increasing concern among health care workers of contamination from the body fluids of patients.

SUMMARY OF THE INVENTION

The principal purpose of the invention is to reduce exposure to urine when manipulating or repositioning the urinary drainage bag outlet tube. The aseptic drainage outlet device of the invention allows an individual to disconnect the outlet tube from its secure parked position without fear of residual droplets of urine being "flicked" on the user's hands or face due to the spring-like action normally resulting from the inherent elastic resiliency of the tube.

This control over the tube is effected utilizing a coupler which includes a connector mounted on the distal or discharge end of the tube, rigidifying the end portion of the tube and forming a rigid hollow cylindrical extension thereof. The connector releasably locks or couples to the bag-mounted housing. Disengagement of the connector from the housing utilizes a positive manual grasping and manipulation of the connector in a manner which, in conjunction with the construction of the connector, both controls and inhibits any tendency for the tube end portion to flick or otherwise resiliently snap as it is withdrawn from the housing.

The coupler connector comprises an elongate hollow cylindrical or tubular body having an inlet end portion frictionally telescoped within the distal end portion of the outlet tube. The connector body further includes a discharge end portion which extends linearly beyond the outlet tube, defining a rigid extension which is selectively received, in a substantially sealed manner, within a bag mounted housing.

The connector is secured to the housing by a pair of longitudinally extending diametrically opposed pivot bars or arms which are integrally pivoted to the connector body at approximately mid-point along the length thereof. The arms include rearwardly extending opposed lever portions which overlie the distal discharge end of the outlet tube whereby a grasping and manipulation of these lever portions also involves a simultaneous gripping of the tube end portion. The arms also include forwardly extending gripping portions which engage to the opposite sides fo the housing upon the insertion of the connector body therein. The gripping portions terminate in laterally inwardly directed rigid fingers which engage behind a shoulder portion about the housing in a manner whereby a radial outward movement of the fingers is required to release the connector for withdrawal from the housing. The bars or arms, in the at-rest or relaxed position thereof, position the fingers for engagement behind the housing shoulder. An outward springing of the gripping portions of the arm is required to both engage and disengage the connector. Upon release of pressure on the arms, the arms, through the inherent memory of the material of the connector, automatically return to the at-rest position.

Polypropylene is a preferred material for the connector due to its ability to be flexed numerous times without distortion, and because of the memory characteristics thereof. This material is also preferred in light of its ability to withstand the heat of sterilization without distortion, and its imperviousness to chemicals used in hospital environments. It is also economical and widely used in injection molding. Another, although more costly, material is ABS.

Other features and advantages of the invention will become more apparent from the more detailed description following hereinafter.

DESCRIPTION OF THE PREFERRED EMBODIMENT

Figure 1:
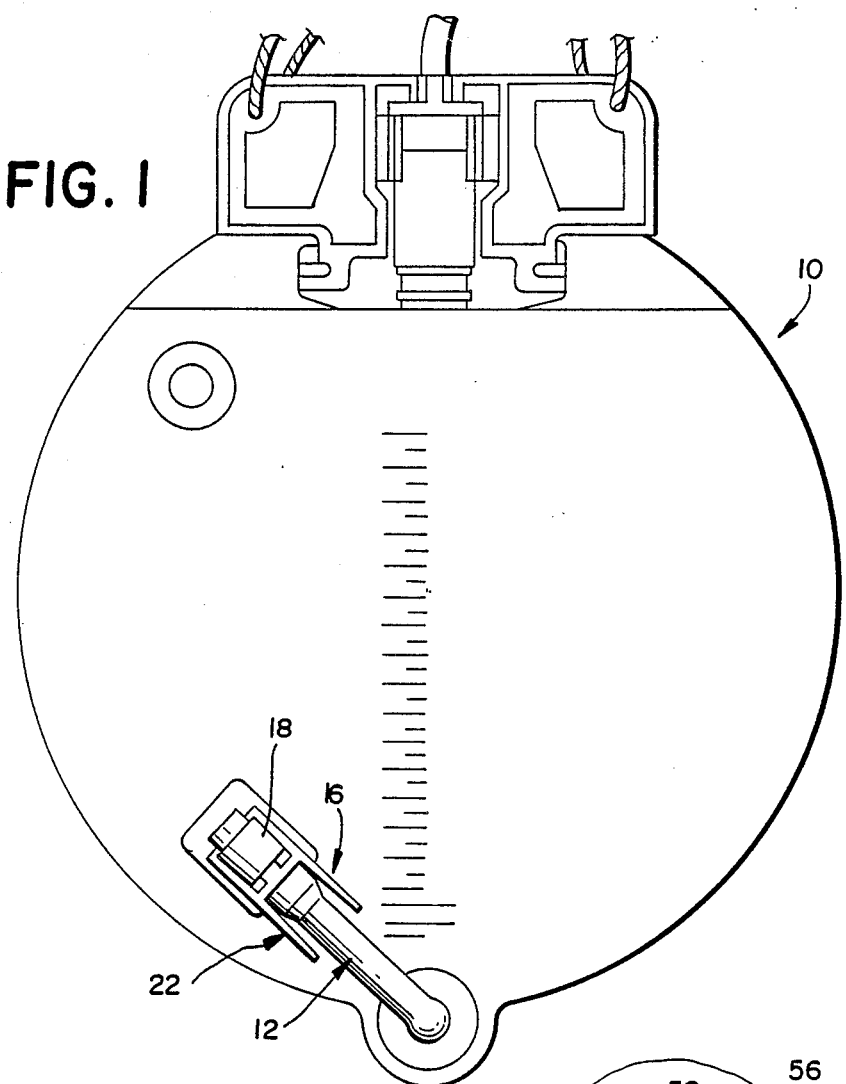
FIG. 1 is an elevational view of a drainage bag with the tube locking and manipulation system of the invention incorporated therein.
Figure 5:
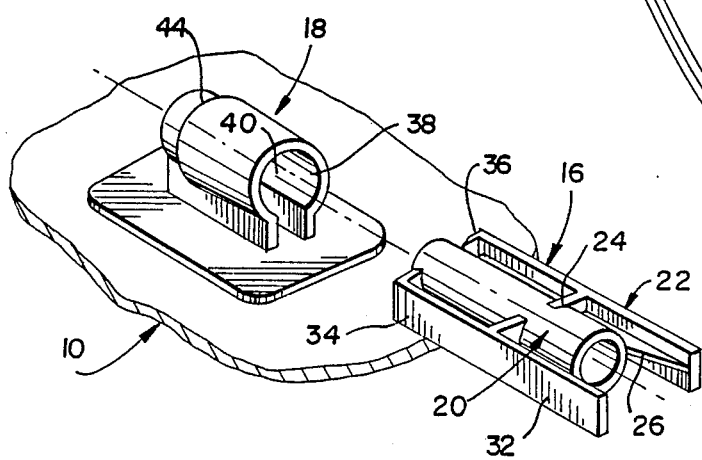
FIG. 5 is an exploded perspective view of the connector and housing.

Referring now more specifically to the drawings, reference Numeral 10 is used to designate a conventional flexible urine drainage bag incorporating an elongate elastomeric outlet tube 12 mounted with one end thereof in sealed communication with the low point of the bag 10. The distal or outer discharge end of tube 12 is, in the conventional drainage bag, telescopically received in a substantially sealed manner in a housing affixed to the wall of the bag at a point above the bag-communicating inner or proximal end of the tube.

In the present invention, the distal end portion 14 of the tube 12 mounts a connector 16 which in turn releasably locks to a complementarily configured housing 18 to define a coupling.

The connector, preferably injection molded of polypropylene, includes a substantially rigid hollow cylindrical or tubular body 20.

Figure 3:
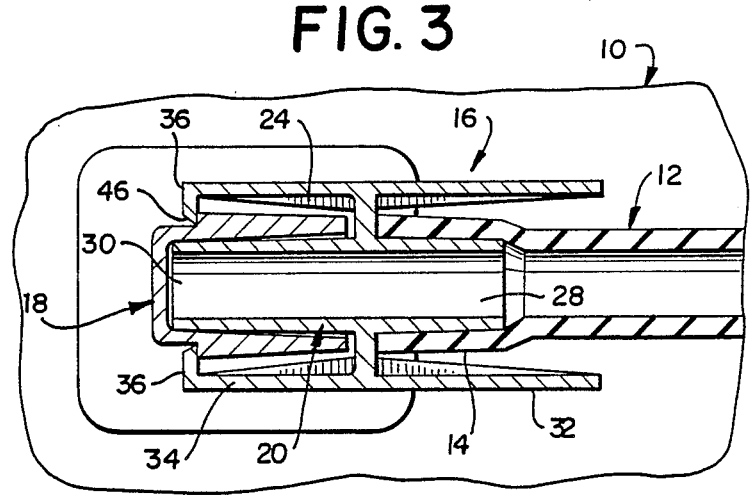
FIG. 3 is a longitudinal sectional view through the structure of FIG. 2 with the connector engaged with the housing.
Figure 4:
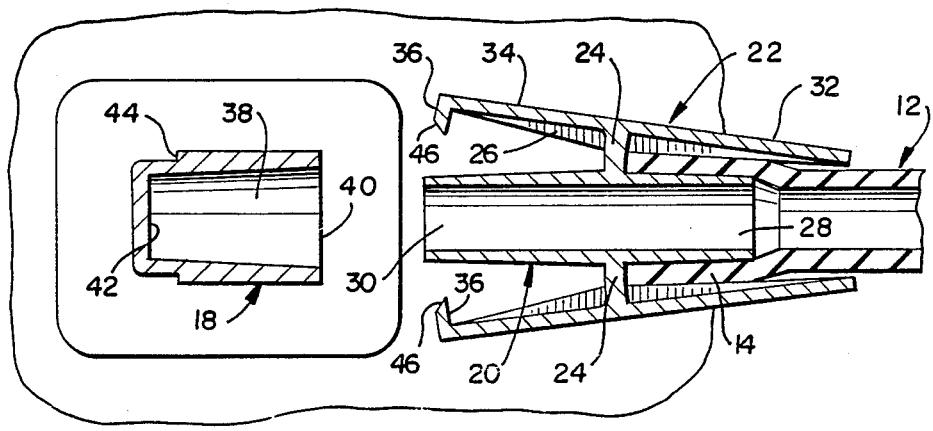
FIG. 4 is a longitudinal cross-sectional view similar to FIG. 3 with the connector disengaged from the housing.

A pair of elongate rigid bars or arms 22 parallel the body 20 in outwardly spaced relation to diametrically opposed sides of the body 20. Each arm, at an intermediate point along the length thereof, is integrally joined to the body 20 at an intermediate point along the length of the body by a joinder or link 24. The links 24 are sufficiently resilient, in the manner of a living hinge, to allow for a manual pivoting of the arms as suggested in FIG. 4. The arms 22 also possess sufficient elastic memory to return the arms 22, after release of manual pressure, to the position of FIG. 3, paralleling the body 20.

The connector arms 22 are flat members reinforced, on the inner surfaces thereof, by central ribs 26 which, with regard to each arm 22, are provided as an aligned pair tapering outward from a maximum thickness at the intermediate link 24 and terminating adjacent the outer opposed ends of the arm.

The connector body 20 includes a mounting portion 28 rearward of the links 24 which is telescopically received within the discharge end portion 14 of the outlet tube 12. The tube 12 preferably seats directly against the links 24 to ensure a complete mounting of the connector 16. The body also includes a forward or discharge portion 30 which is adapted to engage within the housing 18.

The opposed arms 22 each includes a rearwardly extending lever portion 32 which projects beyond the body portion 28 to define elongate finger grips for manipulation of the arms and to allow for a positive gripping of the outlet tube 12. The arms 22 also include forwardly extending gripping portions 34, each of which terminates in an inwardly directed locking finger or flange 36. The fingers 36 are positioned immediately inward of the extreme forward end of the discharge portion 30 of the body 20.

The housing 18 is preferably formed of PVC and dialectrically sealed to the wall of the bag 10 above and to one side of the point of communication between the tube 12 and the bag. The housing 18 includes an elongate bore or socket 38 therein which tapers rearwardly from an open end 40 to a closed inner end 42. The bore is dimensioned and configured to snugly telescopically receive the discharge portion 30 of the connector body 20 in a generally sealed relationship.

The exterior of the housing 18 tapers rearwardly from the open end 40 of the socket 38 and defines a generally conical housing exterior terminating in a shoulder 44 arcuately about the housing slightly forward of the closed end 42. The conical exterior of the housing 18 forms a ramp-like surface which facilitates an engagement of the connector 16 therewith in that the inwardly directed fingers 36 of the arms 22 will engage and slide along the exterior surface as the connector body 20 is introduced into the socket 38, resulting in a spreading of the gripping portions 34 of the arms 22 against the spring action of the integral links 24 until such time as the fingers 36 pass beyond the shoulders 44. At that point, due to the memory characteristics of the arms 22, the fingers 36 will snap behind the shoulders 44 and lock the connector against withdrawal from the housing until such time as a positive manual release is effected.

Incidently, in order to facilitate the movement of the connector into locked engagement with the housing, it will be noted that the inner ends of the fingers 36, along the forward or leading edges 46 thereof, are slightly beveled. Further, the extension of the discharge portion 30 of the body 20 slightly forward of the fingers 36 facilitates an alignment of this tubular body 20 with the housing socket 38 for telescopic movement therein. It is contemplated that the length of the discharge portion 30 of the connector body 20 be slightly longer than the depth of the housing socket 38 so as to provide for a snug seating of the leading end of the discharge portion 30 at the inner end of the socket 38.

Manual release of the connector requires a firm grasping of the discharge end portion of the tube 12 and a positive finger manipulation of the lever portions 32 of the fingers 22. This, in turn, particularly in conjunction with the rigidity at the discharge end defined by the connector body 20, allows for a withdrawal of the outlet tube 12 without any accidental flipping or snapping of the tube end such as could produce an undesirable and uncontrolled discharge of any residual droplets of urine. The actual drainage of the bag is, in a conventional manner, controlled by an appropriate shut-off clamp (not shown) mounted on the outlet tube 12 intermediate the length thereof. Both the coupler of the present invention and the conventional shut-off clamp can be operated by the same hand of the user, thus leaving the other hand free for positioning a collection receptacle or the like.

Figure 6:
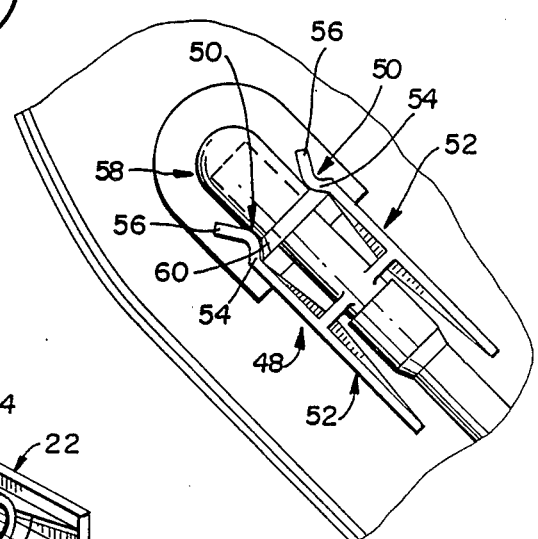
FIG. 6 illustrates a variation of the connector engaged with a conventional housing.
Figure 2:
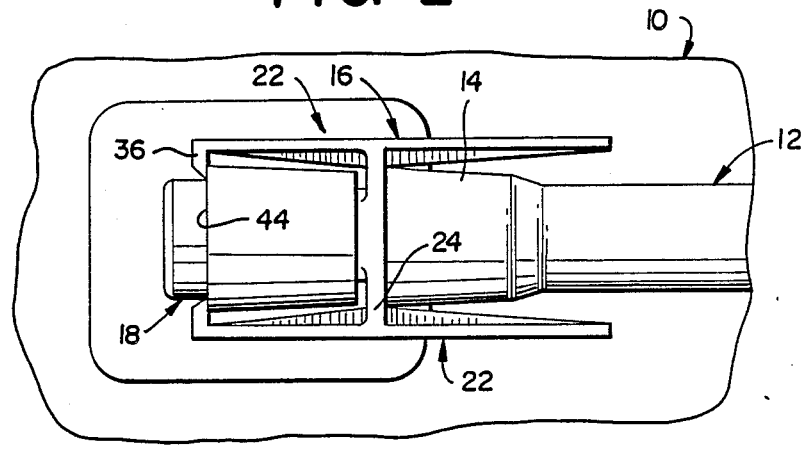
FIG. 2 is an enlarged plan view of the coupling system with the connector tube-mounted and engaged with the housing.

Noting FIG. 6, the connector 48 therein differs in that the gripping fingers 50 are formed as inwardly angled bends in the respective arms 52. Each finger is defined by a first portion 54 inwardly angled at approximately 45° to the respective arm 52, and a second portion 56 outwardly angled from the first portion 54 at approximately 90° to define a forwardly directed camming face.

The housing 58 is of substantially conventional shape and includes a slightly flared tube-guiding flange 60 about the open end. The connector 48 can engage with the housing by merely an inward movement of the connector with the angled fingers 50 camming over the flange 60 for engagement therebehind.

The coupler of the invention provides for a positive securement of the outlet tube within the housing against any possibility of accidental, casual or unplanned release during use of the drainage bag. In addition, the coupler, and in particular the connector, encourages a positive manual grasping of the connector within the hand and a manipulation of the gripping means in a specific manner to effect a release of the outlet tube for withdrawal from the housing. Through a continuous engagement of the hand with the substantially rigid connector, the discharge end of the outlet tube is at all times controlled by the user, thus effectively precluding substantially any possibility of a flicking action as commonly experienced in the conventional elastomeric outlet tube without the coupler means of the invention.

While not illustrated, the present invention also contemplates the possibility of the connector being engagable with an appropriate mating drainage tube or receptacle incorporating a tubular end for reception of the discharge portion of the connector body, and shoulder means for releasable engagement of the connector fingers therewith, thereby further reducing contamination potential.

We claim:

1. A urinary drainage bag with an elastomeric outlet tube, said tube having a first end in fluid receiving communication with the bag and a second remote fluid discharge end, coupling means for releasably locking the tube discharge end to the bag, said coupling means comprising a housing mounted on said bag for releasably securing said discharge end of said tube, and connector means for rigidifying said discharge end and for requiring a positive manual grasping of the rigidified tube discharge end for release and removal from said housing and for precluding free movement of said discharge end when released said housing, said connector means including a rigid elongate hollow body having a mounting end portion telescopically engaged with and rigidifying said tube discharge end, and a forward free end portion extending beyond said tube discharge end, and elongate arms parallel to said hollow body in outwardly spaced relation to opposed sides thereof, said arms including forward gripping portions terminating in gripping fingers laterally directed inward toward the free end portion of the hollow body, means for mounting said arms on said hollow body for selective manual movement of said gripping fingers laterally away from and toward said hollow body, said housing having a socket therein with an open outer end and a closed inner end, the free end portion of said hollow body being slidably receivable in said socket through the open outer end thereof, said housing including shoulder means thereon, said gripping fingers engaging said shoulder means upon reception of said hollow body within said socket, said arms including integral rear lever portions overlying the mounting end portion of the hollow body and defining hand manipulable release means exterior of the housing, said release means requiring a positive manual grasping of said hollow body and a manual force on said release means to release said discharge end from said housing for preventing accidental discharge of fluid droplets caused by release of said discharge end from said housing, whereby a positive manual control is constantly maintained on the rigidified discharge end of the elastomeric tube as said tube discharge end is released from said housing.

2. The bag of claim 1 wherein the free end portion of the connector hollow body extends beyond the laterally directed gripping fingers for facilitating alignment of the free end portion of the body with the socket as the body is slidably received within the socket.

3. The bag of claim 2 wherein the housing includes a tapered exterior between the open end of the socket and said shoulder means.

* * * * *